(12) United States Patent
Poole et al.

(10) Patent No.: US 6,658,080 B1
(45) Date of Patent: Dec. 2, 2003

(54) DISPLAYING IMAGE DATA USING AUTOMATIC PRESETS

(75) Inventors: Ian Poole, Edinburgh (GB); Andrew John Bissell, Edinburgh (GB)

(73) Assignee: Voxar Limited, Edinburgh (GB)

( * ) Notice: Subject to any disclaimer, the term of this patent is extended or adjusted under 35 U.S.C. 154(b) by 0 days.

(21) Appl. No.: 10/212,363

(22) Filed: Aug. 5, 2002

(51) Int. Cl.$^7$ .................................................. A61B 6/03
(52) U.S. Cl. ............................................ 378/4; 378/94
(58) Field of Search ............................ 378/4, 8, 15, 19, 378/901

(56) References Cited

U.S. PATENT DOCUMENTS 6,343,936 B1 * 2/2002 Kaufman et al. ............ 434/262
6,514,082 B2 * 2/2003 Kaufman et al. ............ 434/262

OTHER PUBLICATIONS

Zack, G.W. et al. "Automatic Measurement of Sister Chromatid Exchange Frequency." *The Journal of Histochemistry and Cytochemistry.* 27.7 (1977) 741–753.

* cited by examiner

*Primary Examiner*—David V. Bruce
(74) *Attorney, Agent, or Firm*—Renner, Otto, Boisselle & Sklar, LLP

(57) ABSTRACT

A computer automated method for setting visualization parameter boundaries in a preset for displaying an image from a 3D data set applicable to magnetic resonance (MR) data, computer tomography (CT) data and other 3D data sets obtained in medical imaging is described. In one example the visualization parameter boundaries are color boundaries. A histogram of data values of voxels within a user-selected volume of interest (VOI) is generated and an analysis of a convex hull spanning the histogram is made to provide one or more visualization thresholds which divide the histogram into sub-regions. The sub-regions relate to different tissue types within the VOI and color boundaries are set based on the visualization thresholds for displaying the different tissue types in different colors. The method allows color boundaries in a preset to be set objectively and automatically so that images can be displayed consistently and with less user manipulation. The method may also provide a measure of the significance of each color boundary in the preset to assist a user in interpreting a displayed image.

26 Claims, 11 Drawing Sheets

(6 of 11 Drawing Sheet(s) Filed in Color)

DISPLAYING IMAGE DATA USING AUTOMATIC PRESETS

BACKGROUND OF THE INVENTION

The invention relates to the setting of visualization parameter boundaries, such as color and opacity boundaries, for displaying images, in particular two-dimensional (2D) projections from three-dimensional (3D) data sets.

When displaying an image, such as in medical imaging applications, it is known to associate particular signal values with particular colors and opacities (known as visualization parameters) to assist visualization. This mapping is done when using data from a 3D data set (voxel data set) to compute a 2D data set (pixel data set) representing a 2D projection of the voxel data set for display on a computer screen or other conventional 2D display apparatus. This process is known as rendering.

The 2D data set is more amenable to user interpretation if different colors and opacities are allocated to different signal values in the 3D data set. The details of the mapping of signal values to colors and opacities are stored in a look-up table which is often referred to as the RGBA color table (R, G, B and A referring to red, green, blue and alpha (for opacity) respectively). The color table can be defined such that an entire color and opacity range is uniformly distributed between the minimum and maximum signal values in the voxel data set, as in a gray scale. Alternatively, the color table can be defined by attributing different discrete colors and opacities to different signal value ranges. In more sophisticated approaches, different sub-ranges are ascribed different colors (e.g. red) and the shade of the color is smoothly varied across each sub-range (e.g. crimson to scarlet).

When displaying data such as in medical imaging, the signal values comprising the data set do not usually correspond to what would normally be regarded as visual properties, such as color or intensity, but instead correspond to detected signal values from the measuring system used, such as computer-assisted tomography (CT) scanners, magnetic resonance (MR) scanners, ultrasound scanners and positron-emission-tomography (PET) systems. As an example, signal values from CT scanning will represent tissue opacity, i.e. X-ray attenuation. In order to improve the ease of interpretation of such images it is known to map different colors and opacities to different ranges of display value such that particular features, e.g. bone (which will generally have a relatively high opacity) can be more clearly distinguished from soft tissue (which will generally have a relatively low opacity).

When displaying a 2D projection of a 3D data set, in addition to attributing distinct ranges of color to voxels having particular signal value ranges, voxels within the 3D data set may also be selected for removal from the projected 2D image to reveal other more interesting features. The choice of which voxels are to be removed, or sculpted, from the projected image can also be based on the signal value associated with particular voxels. For example, those voxels having signal values which correspond to soft tissue can be sculpted, i.e. not rendered and therefore "invisible", thereby revealing those voxels having signal values corresponding to bone which would otherwise be visually obscured by the soft tissue.

The determination of the most appropriate color table (known in the art as a preset) to apply to an image derived from a particular 3D data set is not trivial and is dependent on many features of the 3D data set. For example, the details of a suitable color table will depend on the subject, what type of data is being represented, whether (and if so, how) the data are calibrated and what particular features of the 3D data set the user might wish to highlight, which will depend on the clinical application. It can therefore be a difficult and laborious task to produce a displayed image that is clinically useful. Furthermore, there is inevitably an element of user-subjectivity in manually defining a color table and this can create difficulties in comparing and interpreting images created by different users, or even supposedly similar images created by a single user. In addition, the user will generally base the choice of color table on a specific 2D projection of the 3D data set rather than on characteristics of the overall 3D data set. A color table chosen for application to one particular projected image will not necessarily be appropriate to another projection of the same 3D data set. A color table which is objectively based on characteristics of the 3D data set rather than a single projection would be preferred.

Accordingly, there is a need in the art for a method of automatically determining appropriate color table presets when displaying medical image data.

SUMMARY OF THE INVENTION

According to the invention there is provided a method of setting visualization parameter boundaries for displaying an image from a 3D data set comprising a plurality of voxels, each with an associated signal value, comprising: selecting a volume of interest (VOI) within the 3D data set; generating a histogram of signal values from voxels that are within the VOI; applying a numerical analysis method to the histogram to determine a visualization threshold; and setting at least one of a plurality of boundaries for a visualization parameter according to the visualization threshold.

By restricting the histogram to voxels taken from the VOI, a numerical analysis method can be applied to the histogram which is sensitive to subtle variations in signal value and can reliably identify significant boundaries within the 3D data set for visualization. This allows the visualization parameter boundaries to be set automatically, which is especially useful for 3D data sets for which the signal values have no calibration, as is the case for MR scans.

In some embodiments, a first visualization parameter boundary is set at the visualization threshold. In other embodiments, first and second visualization parameter boundaries are set either side of the visualization threshold. This latter approach can be advantageous if an opacity curve interpolation algorithm is used to calculate an opacity curve between the visualization parameter boundaries.

The numerical analysis method may be applied once to determine only one visualization threshold. Remaining visualization parameter boundaries can then be set manually. Alternatively, the numerical analysis method can be applied iteratively to the histogram to determine a plurality of visualization thresholds and corresponding visualization parameter boundaries.

A significance test may be applied to visualization thresholds and, according to the outcome of the significance test, a significance marker can be ascribed for those ones of the voxels having signal values at or adjacent the visualization threshold, wherein the significance marker indicates significance or insignificance of the visualization threshold.

If two visualization parameter boundaries are set, one each side of the visualization threshold, and the visualization threshold is determined to be significant, then it is convenient to mark as significant only the voxels having signal values at one of the two visualization parameter boundaries. In one example, if a visualization threshold is calculated by the numerical analysis method to lie at a signal value of 54, and visualization parameter boundaries are set at 54±3, i.e. at 51 and 57, then the voxels with signal values of 57 can be marked as significant, and the voxels with signal values of 51 as insignificant.

The significance test can be used to distinguish between visualization parameter boundaries used as enhancements to visualizations of a single tissue type (known as cosmetic boundaries) and those used to identify different tissue-types for the purpose of segmentation (known as significant boundaries). Accordingly, the method may further comprise applying a selection tool to the 3D data set, wherein the selection tool is sensitive to the significance markers. One or more of the selection tools can be designed to ignore voxels that have been marked as insignificant.

The rate of change of a visualization parameter across a visualization parameter boundary may also be modified based on the significance of the visualization parameter boundary. A sharpness parameter can be calculated for determining what rate of change of the visualization parameter to apply at a boundary.

In some embodiments of the invention, the sharpness parameter is the same as the significance marker. The sharpness need not simply be a binary operand, but can adopt a range of integer values, for example from 0 to 100. A sharpness of zero indicates an insignificant boundary, which is referred to as a cosmetic boundary in view of its irrelevance to selection tools. A sharpness of 100 indicates a boundary that has the maximum degree of significance. Intermediate values are used to indicate intermediate significance. In addition to affecting the blending of visualization parameters, the non-zero values may be used for filtering by the selection tools so that boundaries with a significance value of, for example, 5 are significant to some but not all selection tools, a boundary with a significance value of 50 is significant for a greater subset of the selection tools, and a boundary with the maximum significance value of 100 is significant to all selection tools. Alternatively, the non-zero significance values may be used by selection tools to resolve conflicts between different marked boundaries, with boundaries having higher significance values taking precedence. Examples of selection tools are tools for marking objects in a set of connected or unconnected voxels with a visualization parameter (e.g. color or opacity) between two significant visualization parameter boundaries, multiple groups of connected or unconnected voxels above a significant boundary or multiple bands of connected or unconnected voxels below a significant boundary. Marked voxels could then, for example, be sculpted. Sculpting is a well known term of art used to describe voxels that are marked to be transparent from view irrespective of their signal values.

In the best mode of the invention, the numerical analysis method comprises: forming a convex hull of a plurality of segments around the histogram; determining which perpendicular from the segments to the histogram has the greatest length; and taking the signal value at the intersection between the histogram and the perpendicular as the visualization threshold. The sharpness value and the significance test can then be based on the length of the perpendicular determined to have the greatest length. For example, the visualization threshold can be determined to be insignificant if the ratio of the length of the perpendicular to a parameter derived from the signal value range and/or the frequency range of the histogram is below a minimum score.

For some automatic presets, the numerical analysis method is applied to the histogram within a predetermined restricted range of signal values to search for a visualization threshold within that restricted range. This will be particularly useful for 3D data sets with calibrated signal values, such as X-ray data sets calibrated in Hounsfield units. Accordingly, the restricted range may be defined in terms of Hounsfield units.

To provide the user with information about the nature of the automatically calculated thresholds, the histogram and its visualization parameter boundaries can be displayed to the user together with the image created from the 3D data set, thus making the user aware of the visualization parameter boundaries determined by the automatic preset.

The method of the invention is particularly powerful in that it can take account of sculpting performed on the 3D data set prior to automatic preset determination according to the invention. A common example of sculpting will be when a plane is defined through a 3D data set and all voxels to one side of the plane are not rendered, irrespective of their signal values. Another example of sculpting will be the removal of a given set of connected voxels with signal values in a specified range, thus restricting the range of signal values to be visualized prior to determining an automatic preset. Sculpting can be taken account of by restricting the histogram to unsculpted voxels in the VOI.

It has been recognized that voxels with the highest and lowest signal values often constitute bad data which can skew the results of the numerical analysis of the histogram. Accordingly, it is preferred that voxels with the highest and/or the lowest signal values are excluded from the numerical analysis method. For example, the voxels with the lowest and highest 0.1% of the signal values can be excluded. Other proportions could also be envisaged.

In some implementations the method may operate interactively. In such cases, if a user re-defines the VOI, the method of setting visualization parameter boundaries is automatically reapplied to continuously provide the most appropriate visualization parameter boundaries.

The invention further provides a computer program product bearing computer readable instructions for performing the method of the invention.

The invention also provides a computer apparatus loaded with computer readable instructions for performing the method of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

For a better understanding of the invention and to show how the same may be carried into effect reference is now made by way of example to the accompanying drawings in which:

FIG. 2b schematically shows a graphical representation of the color and opacity curve mappings used in generating the 2D image shown in FIG. 2a;

FIG. 7b shows an example image displayed according to the automatic preset of FIG. 7a;

FIG. 8b shows an example image displayed according to the automatic preset of FIG. 8a;

FIG. 9b shows an example image displayed according to the automatic preset of FIG. 9a.

DETAILED DESCRIPTION

Figure 1:
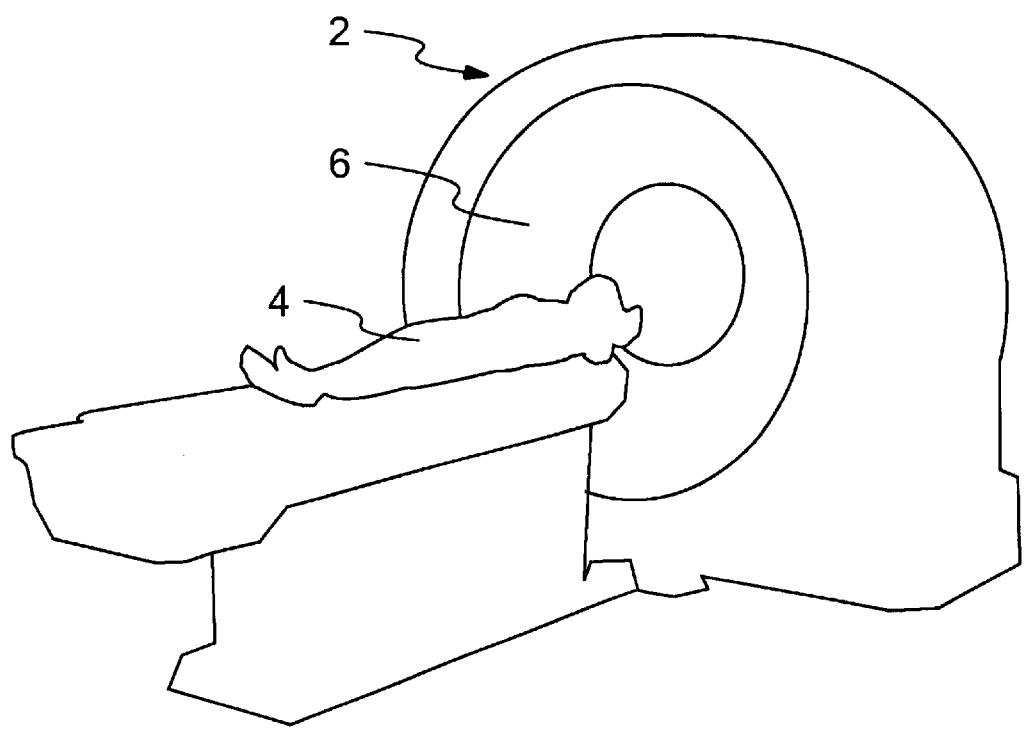
FIG. 1 shows a generic computer tomography scanner for generating a 3D data set.

FIG. 1 is a schematic perspective view of a generic CT scanner 2 for obtaining a 3D scan of a region of a patient 4. An anatomical feature of interest (in this case a head) is placed within a circular opening 6 of the CT scanner 2 and a series of X-ray exposures is taken. Raw image data is derived from the CT scanner and could comprise a collection of one hundred 2D 512*512 data subsets, for example. These data subsets, each representing an X-ray image of the region of the patient being studied, are subject to image processing in accordance with known techniques to produce a 3D representation of the feature imaged such that various user-selected 2D projections of the 3D representation can be displayed (typically on a computer monitor). The techniques for generating such 3D representations of structures from collections of 2D data subsets are known and will not be described further herein.

Figure 2A:
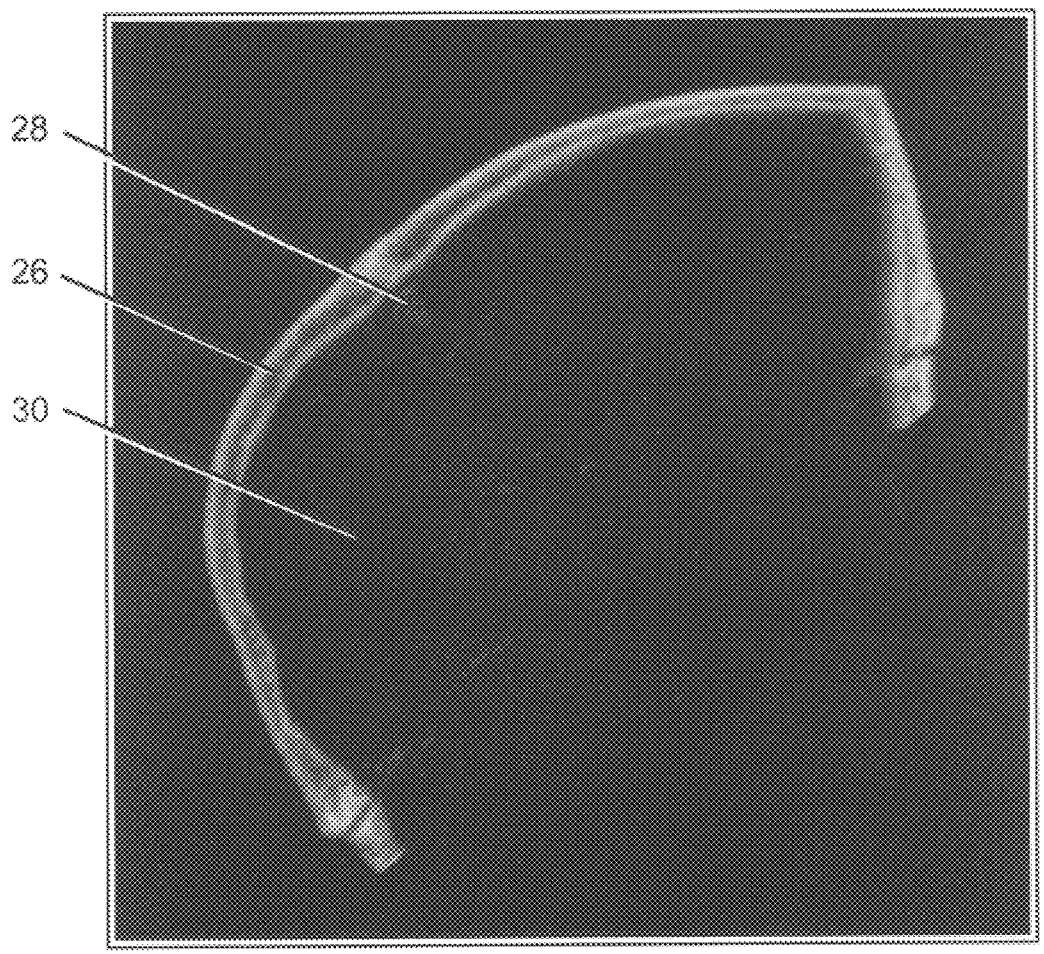
FIG. 2a shows a 2D projection of a 3D data set with tissue opacity values being represented by a linear gray-scale.
Figure 2B:
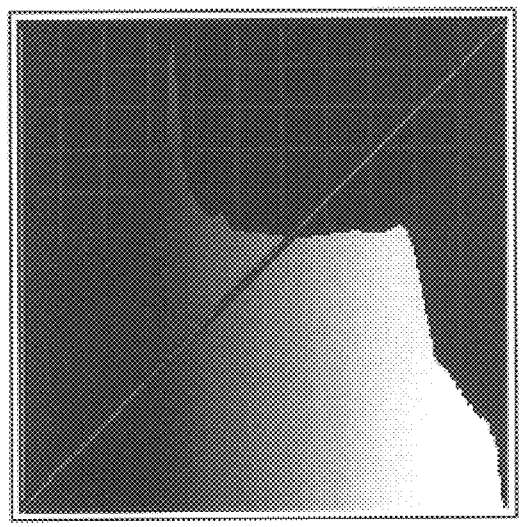
Figure 2C:
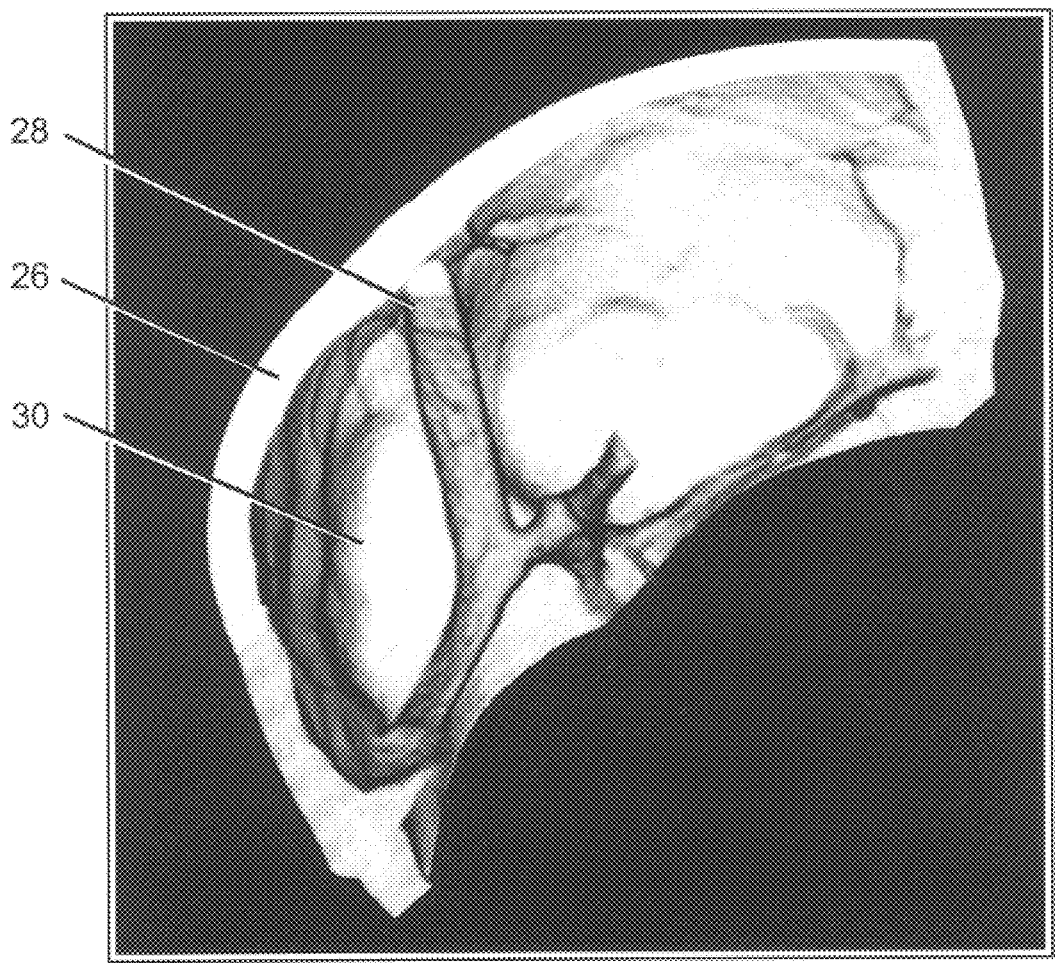
FIG. 2c shows a 2D projection of a 3D data set with ranges of tissue opacity values being represented by ranges of a gray-scale defined by presets.
Figure 2D:
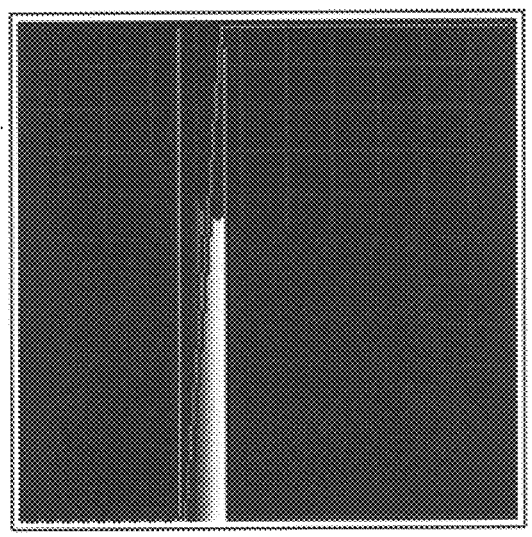
FIG. 2d schematically shows a graphical representation of the color and opacity curve mappings used in generating the 2D image shown in FIG. 2c.
Figure 2E:
FIG. 2e shows a 2D projection of a 3D data set with ranges of tissue opacity values being represented by ranges of colors defined by presets.

FIGS. 2a, 2c and 2e show example 2D images of the same projection from a 3D CT data set but with different presets.

FIGS. 2b and 2d show graphical representations of the color and opacity curve mappings used in generating the 2D images shown in FIGS. 2a and 2c respectively. FIGS. 2a–e are included to illustrate the effect of presets on such images before describing how presets are implemented in specific embodiments of the invention.

FIG. 2a shows an example 2D image which is a projection of a 3D data set obtained from a CT scanner. A VOI within the 3D data set has been selected for display. The material surrounding the VOI is not rendered in the projection. The image is displayed with a uniform gray-scale ranging from black to white.

FIG. 2b schematically shows a graphical representation of the color and opacity curve mappings used in generating the 2D image shown in FIG. 2a. FIG. 2b includes a plot of a binned frequency distribution of the signal values in the VOI with a superposed line plot of opacity as a function of signal value (red curve). The shading of the area under the binned frequency distribution plot indicates the mapping of colors to signal value in the rendering.

There are three tissue types in the projected image. These are a region of bone 26, a region of soft tissue 30 and a barely visible network of blood vessels 28. The high X-ray stopping power of bone, compared to that of blood and soft tissue, makes the region of bone 26 easily identifiable in the image due to the high opacity associated with the associated voxels. However, since the opacities of blood and soft tissue are more similar, they are not as clearly distinguished. In particular, it is difficult to see the blood vessel network.

FIG. 2c shows a 2D image of the same projection as FIG. 2a, but rendered with a different color and opacity mapping, i.e. a different preset.

FIG. 2d schematically shows a graphical representation of the color and opacity curve mappings used in generating the 2D image shown in FIG. 2c. FIG. 2d includes a plot of a binned frequency distribution of the signal values in the VOI and a superposed line plot of opacity as a function of signal value (red curve). The shading of the area under the binned frequency distribution plot again indicates the mapping of colors to signal values in the rendering.

In FIG. 2c, signal values indicative of soft tissue voxels have been colored significantly differently from signal values indicative of blood vessel voxels. This makes the interpretation of the blood vessels much clearer. In practice, however, a wider range of colors will be available than can be reliably shown in a black-and-white figure such as FIG. 2c, and the three tissue types could be shown in distinctly different colors.

FIG. 2e shows a 2D image of the same projection as FIGS. 2a and 2b, but rendered with a different color and opacity mapping, i.e. a different preset. FIG. 2e shows the signal values of the voxels within the VOI (and hence the corresponding portions in the projected image) as different colors. Voxels associated with the blood vessel network are shaded yellow, those of the soft tissue are allocated shades of transparent red and those of the bone are allocated shades of cream.

The range of displayable colors and opacities to which the voxel signal values are to be mapped (i.e. the entries in the color table) will in general depend on the specific application. For example, in one application images might be represented using five color ranges with the color ranges being black, red, orange, yellow and white. The opacity level from black to white might range from 0% to 100% opacity with the colors mixing in relation to the opacity curve. This would allow for a smooth transition between bands, with the color and opacity values at the upper edge or boundary of one range matching the color and opacity values at the lower edge of boundary of the adjacent range. In this way, the five ranges blend together at their boundaries to form a smoothly varying and continuous spectrum. The colors at the bottom boundary of the first range and the top boundary of the fifth range are black and white respectively.

Each of these five color ranges can be mapped to the voxel signal values which represent different tissue types to distinctly identify the different tissues. For example, bone might be represented in shades of cream, blood in shades of yellow, a kidney in shades of orange and so on, all with varying opacities. The task of attributing color and opacity to different tissue types becomes one of determining suitable signal values, hereafter referred to as visualization thresholds, for defining boundaries between the ranges.

Sub-ranges of signal values between color boundaries may be taken to represent different tissue types. The shades of color available within the color range associated with each tissue type can then be appropriately mapped to the sub-range of signal values. For instance, in one example there are 32 shades of cream available for coloring bone, and bone is associated with signal values between 154 and 217 (in arbitrary units). A color look-up table could then associate the first shade of cream with signal values 154 and 155, the second shade of cream with signal values 156 and 157, the third with 158 and 159 and so on through to associating the thirty-second shade of cream with signal values 216 and 217.

Figure 3:
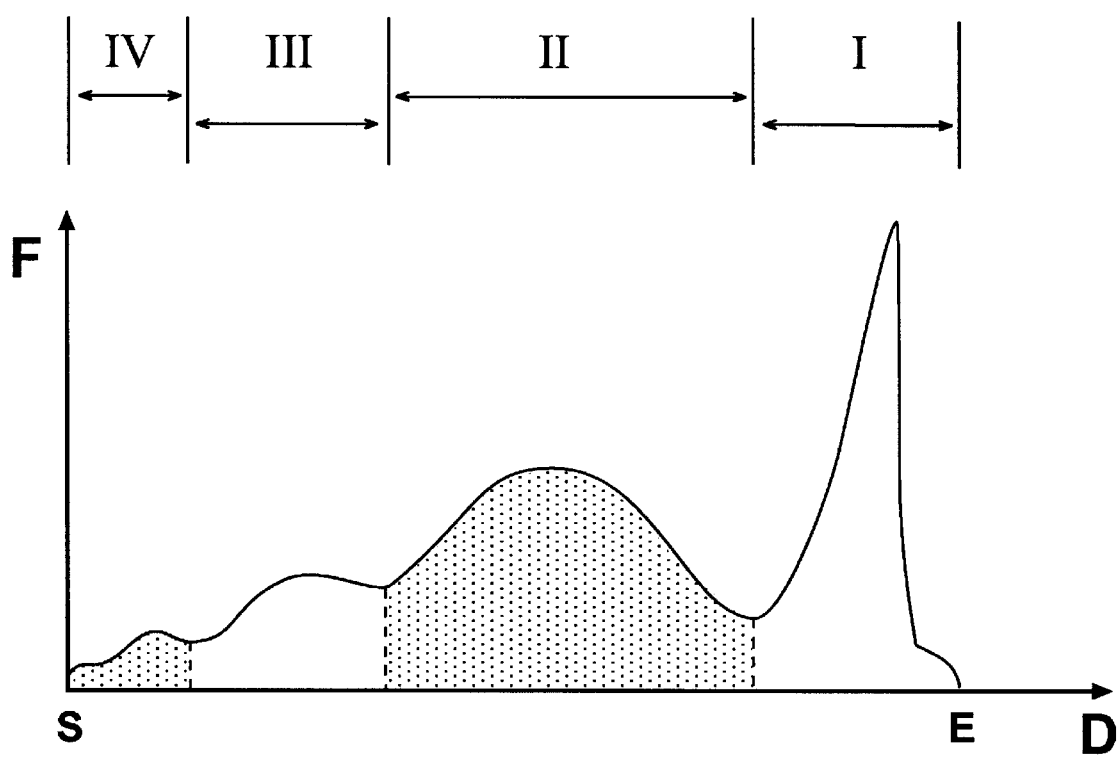
FIG. 3 shows a histogram of data values within a volume of interest (VOI) within a 3D data set.

FIG. 3 is a histogram which schematically shows the binned frequency distribution F of an example set of voxels within a selected VOI as a function of signal value D. The signal values D may be in arbitrary units (typical for MR) or calibrated units (such as Hounsfield units (HU) that are used for CT and other types of X-ray imaging). The histogram shown in FIG. 3 represents the voxels within a VOI from which a 2D projected image (such as those shown in FIGS. 2a, 2c and 2e) can be derived and the signal values represent X-ray attenuation calibrated in HUs.

The signal values D of the voxels within the selected VOI are distributed between a minimum value S and a maximum value E. Within this overall range of signal values, four distinct voxel value sub-ranges are evident. A first voxel value sub-range I has a narrow peak at relatively high signal values, a second voxel value sub-range II has a relatively broad peak, a third voxel value sub-range III has a shoulder on the lower signal value side of the second voxel value sub-range II and a fourth voxel value sub-range IV has a shoulder on the lower signal value side of the third voxel value sub-range III.

The different voxel value sub-ranges I–IV identified in the histogram are likely to relate to different tissue types in the 3D data set and so would benefit from being displayed with different color ranges. For example, one might reasonably infer that sub-range I of high X-ray attenuation corresponds to bone, sub-range II corresponds to blood, sub-range III corresponds to soft tissue and sub-range IV represents the background tissue type or air.

It is not necessary when displaying the images to pre-associate voxel value sub-ranges in the histogram with particular tissue types. In fact, if the signal values in the data set are un-calibrated it may not even be possible to do so from the signal values alone. Nonetheless, if distinct voxel value sub-ranges in the histogram can be identified by a numerical analysis, derived images can be shown with different tissue types clearly and consistently displayed without the need for user-driven post-display processing.

Figure 4:
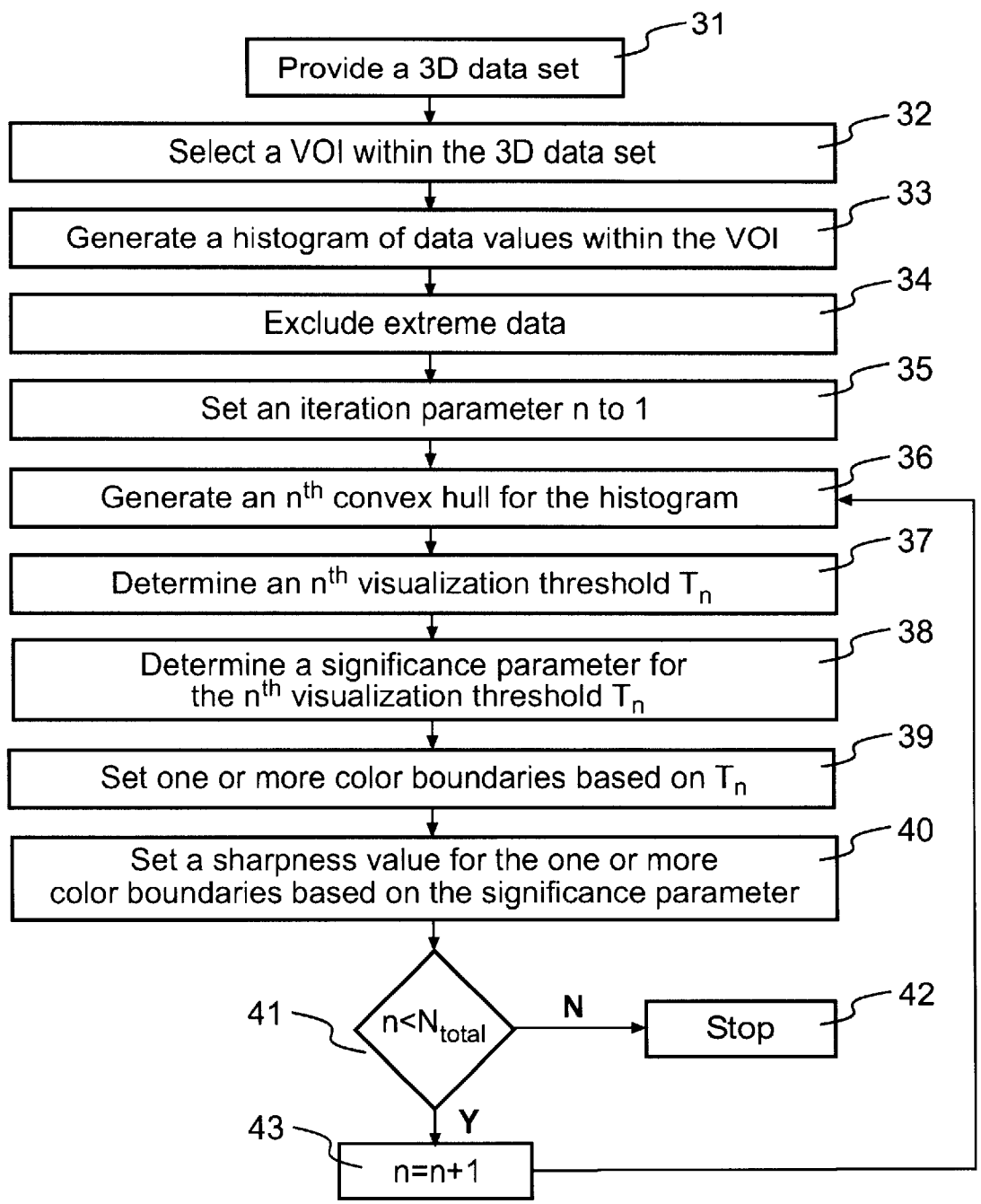
FIG. 4 shows a flow chart of an automatic preset determination method according to an embodiment of the invention.

FIG. 4 is a flow chart showing the steps involved in determining color boundaries for allocating displayable colors based on a numerical analysis of signal values. In a first step 31, a 3D data set of signal values is provided. The 3D data set in this example is provided by an MR scanner and is calibrated in arbitrary units. However, any 3D data set could equally well be used. In a next step 32, a VOI within the data set is selected. This step of selecting a VOI within may be performed manually or automatically, for instance using a connectivity algorithm. In a next step 33, a histogram of the signal values of the voxels within the VOI is generated, such as the one shown in FIG. 3, for example. In a next step 34, a set of extreme signal values are identified. Exclusion of this set of extreme signal values from subsequent steps of the determination of color boundaries helps to avoid any undesirable skewing of the results by signal values which are not considered statistically significant. Such extreme values might be caused by highly attenuating medical implants (such as screws) or defects in the image data set, for example. By ignoring a fraction of the highest and lowest signal values, such as the extreme 0.1% of voxels at each end of the range, any of these extreme outlier voxels within the VOI will not unduly skew the results of the numerical analysis. However, if there are no extreme outlier voxels, the numerical analysis will not be unduly affected by ignoring a relatively small fraction of the histogram. After excluding the extreme data, the histogram is effectively considered to run between signal values L and U, where signal values between S and L, and between U and E are those which are excluded. Whereas in this example a default fraction of extreme voxels are excluded, the fraction discarded could also depend on characteristics of the data set and/or a subject being studied.

In a next step 35, an iteration parameter n is given an initial value of 1. The iteration parameter is indicative of how many visualization thresholds for determining visualization parameters have already being determined, at this stage of the flow chart, a value of n means that n−1 visualization thresholds have previously been found. In a next step 36, an $n^{th}$ convex hull of the histogram is determined. The $n^{th}$ convex hull is defined to be a curve spanning the signal value range L to U and which comprises that series of line segments which combine to form the shortest possible single curve drawn between the histogram values at L and U subject to the condition that at any given signal value within the range, the curve must be greater than or equal to the value of the histogram, and further subject to the condition that the $n^{th}$ convex hull must also meet the histogram profile at all previously identified color boundaries.

Figure 5A:
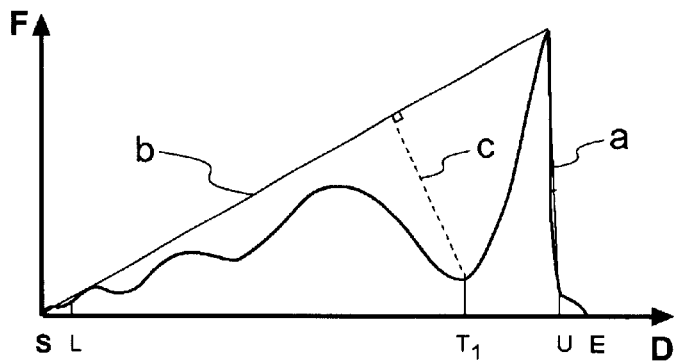
FIG. 5a shows a histogram of data values within a VOI within a 3D data set and to which a first convex hull has been applied to determine a first visualization threshold.

FIG. 5a shows the histogram previously shown in FIG. 3 but on which the first (i.e. $n^{th}$ where n=1) convex hull spanning the histogram has been drawn (since n=1, there are no previously identified color boundaries at which the first convex hull must meet the histogram). It can be seen that the first convex hull contains two extended straight line portions marked b and a. These are the distinct and continuous sections of the first convex hull which deviate from following the histogram profile by "cutting corners" and thereby minimizing the integrated length of the convex hull.

In a next step 37, an $n^{th}$ visualization threshold $T_n$ is found by determining the point on the histogram profile for which the $n^{th}$ convex hull has the maximum nearest distance. This is the point on the histogram from which the longest possible line can be drawn to meet the $n^{th}$ convex hull perpendicularly. This point, which must intersect the $n^{th}$ convex hull on one of its extended straight line portions, can be determined, to a finite accuracy, by a number of known techniques. The longest perpendicular which can be drawn between the first convex hull and the histogram profile shown in FIG. 5a connects to the straight line portion marked b and is indicated in the figure by the dotted-line marked c. This line intersects the histogram profile at signal value $T_1$ and so defines a first visualization threshold of $T_1$. The first visualization threshold $T_1$ divides the histogram into two ranges, one running between signal values L and $T_1$ and one running between signal values $T_1$ and U. It is apparent from FIG. 5a that the range between signal values $T_1$ and U corresponds closely with the first voxel value sub-range I identified in the histogram indicated in FIG. 3.

In a next step 38 shown in FIG. 4, a significance parameter for the $n^{th}$ visualization threshold $T_n$ is determined. The determination of the significance parameter is discussed further below.

In a next step 39, one or more color boundaries are set based on the $n^{th}$ visualization threshold $T_n$. In this example, a single color boundary threshold is set at the data value matching the visualization threshold $T_n$. In other examples, depending on clinical application, and/or the requirements of subsequent visualization tools, it may be preferable to associate two color boundaries with a single visualization threshold. For instance, by setting first and second color boundaries at signal values slightly displaced to the lower and higher signal value side of the signal value of an $n^{th}$ visualization threshold, for example at data values $T_n+/-3$ in arbitrary units, a rapid change in colors and opacities allotted to signal values in the vicinity of the visualization threshold occurs which can help to highlight features of the boundary in a subsequently displayed 2D image.

In a next step 40, a sharpness value is set for each of the one or more color boundaries associated with the $n^{th}$ visualization threshold $T_n$. The sharpness value may be based on the significance parameter of $n^{th}$ visualization threshold $T_n$ and can be used to assist in displaying images. The sharpness value may, for example, range from 0 to 100 and be used to determine a level of color blending between the colors near to a color boundary. Increased color blending can be set to occur at boundaries with relatively low sharpness values. This ensures that low significance boundaries appear less harsh in a displayed image. Conversely, little or no color blending is applied to boundaries with relatively high sharpness values. This ensures high significance boundaries appear well defined in a displayed image. If multiple color boundaries are set according to a single visualization threshold, it may be convenient to associate a sharpness value based on the significance parameter of the visualization threshold with only a single one of the multiple color boundaries, and to set a fixed sharpness value for the other of the multiple color boundaries. Since the sharpness values are based on the significance parameter, sharpness values can also be taken as a measure of the significance of a visualization threshold and associated boundaries. The significance of a boundary may play a role in further processing as discussed further below.

In a next step 41, a test is performed to determine whether additional color boundaries are required. The iteration parameter n, which at this stage of the flow chart indicates how many visualization thresholds have been determined, is compared with the total number ($N_{total}$) of visualization thresholds required. $N_{total}$ will depend on the number of displayable color ranges and how many color boundaries have been set for each of the visualization thresholds. For example, in this case, where all visualization thresholds provide a single color boundary, and if there are five displayable color ranges (hence four color boundaries), four visualization thresholds are required and $N_{total}=4$. However, in another example, a particular application might require a color boundary to be set either side of the first visualization threshold and single color boundaries to be set at each subsequent visualization threshold. In such a case the four color boundaries associated with five displayable color ranges would be set after determining only three visualization thresholds since the first visualization threshold sets two color boundaries, accordingly $N_{total}=3$.

If it is determined that no further color boundaries are required (i.e. $n=N_{total}$), the flow chart follows the N-branch from step 41 to step 42 where the preset determination is complete. If further color boundaries are required (i.e. $n<N_{total}$), the flow chart follows the Y-branch from step 41 to a step 42 where the iteration parameter n is incremented, and then returns to step 36 to continue as described above.

Figure 5B:
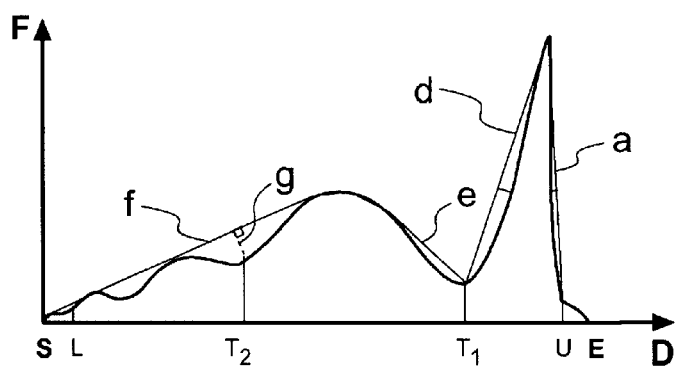
FIG. 5b shows a histogram of data values within a VOI within a 3D data set and to which a second convex hull has been applied to determine a second visualization threshold.

FIG. 5b shows the histogram previously shown in FIG. 3, but on which the data value $T_1$ of the first visualization threshold (and hence in this example also a first color boundary) and the second (i.e. $n^{th}$ where n=2) convex hull are marked (i.e. showing the results of step 36 in the flow chart shown in FIG. 4 during the n=2 iteration). The second convex hull contains four extended straight line portions which are marked f, e, d and a in the figure. In the n=2 iteration of step 37, the point on the histogram from which the longest possible line can be drawn to meet the second convex hull perpendicularly is determined. It is noted that the geometry of the extended line portion marked a in both FIGS. 5a and 5b is not affected by the additional condition applied to the second convex hull (i.e. that it pass through the histogram value at $T_1$). Accordingly it is not necessary to re-calculate the perpendicular distances between this section of the convex hull and the histogram profile since those previously determined may be relied upon.

The longest perpendicular which can be drawn between the second convex hull and the histogram profile shown in FIG. 5b connects to the straight line portion marked f and is indicated in the figure by the dotted-line marked g. This line intersects the histogram profile at signal value $T_2$ which combines with $T_1$ to divide the histogram into three ranges, one running between signal values L and $T_2$, one running between signal values $T_2$ and $T_1$ and, as before, one running between signal values $T_1$ and U. It is apparent from FIG. 5b that the range between signal values $T_2$ and $T_1$ corresponds closely with the second voxel value sub-range II identified in the histogram indicated in FIG. 3. The setting of color boundaries (and their associated sharpness) which are linked to the second visualization threshold $T_2$ will be understood from the above.

Figure 5C:
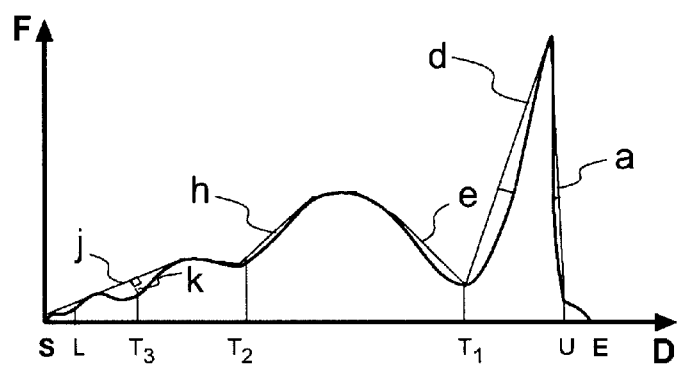
FIG. 5c shows a histogram of data values within a VOI within a 3D data set and to which a third convex hull has been applied to determine a third visualization threshold.

FIG. 5c again shows the histogram previously shown in FIG. 3 but with the third (i.e. $n^{th}$ where n=3) convex hull associated with determining a third visualization threshold $T_3$ also shown. The convex hull in FIG. 5c passes through the histogram values at both $T_1$ and $T_2$ as well as the lower and upper end-points L and U and contains five extended straight line portions marked j, h, e, d, and a. The longest perpendicular which can be drawn between the third convex hull and the histogram profile connects to the straight line portion marked j and is indicated in the figure by the dotted-line marked k. This line intersects the histogram profile at signal value $T_3$ which combines with $T_1$ and $T_2$ to divide the histogram into four ranges, one running between signal values L and $T_3$, one running between signal values $T_3$ and $T_2$, one running between signal values $T_2$ and $T_1$ and one running between signal values $T_1$ and U. It is apparent from FIG. 5c that the ranges between signal values L and $T_3$, and $T_3$ and $T_2$ corresponds closely with the fourth and third voxel value sub-ranges IV, III respectively identified in the histogram indicated in FIG. 3.

As noted above, in the example shown in FIG. 4 the iterative determination of visualization thresholds continues until a pre-set maximum number of associated boundaries have been determined, e.g. if there are five color ranges available for display then four color boundaries are required to define the associated five voxel value sub-ranges within the histogram. When the requisite number of boundaries are determined, the color mappings for displaying images derived from the VOI on which the histogram analysis has been performed can be generated by associating the shades available within each color range with the signal values defined by the color boundaries.

If there are P available color ranges for display and the VOI contains P or more than P distinct tissue types, the method outlined above automatically identifies P voxel value sub-ranges from the histogram of the voxels contained in the VOI. For a given type of data, an appropriate value of P (and hence number of visualization thresholds to be identified) can be selected based on the expected characteristics of the data set.

If, on the other hand, the VOI contains fewer than P distinct tissue types, the allotment of P color ranges will cause more than one color range to be allotted to at least one of the tissue types. A color boundary which is placed within a signal value range representing a single tissue type may appear confusing in the display, especially if the user is unaware of it. As noted above, color blending based on a sharpness value derived from the significance parameter for each visualization threshold can be used to de-emphasize such boundaries.

In addition to setting the sharpness value, the significance parameter may also form the basis of a significance test for determining the significance of a visualization threshold. The significance parameter may, for example, derive from the length of the determined longest perpendicular between the $n^{th}$ convex hull and the histogram. The significance test may require that this longest perpendicular is at least a pre-defined fraction of the histogram's characteristic dimensions. For instance, the significance test may require that the longest perpendicular be at least 5% of the geometric height or width of the histogram. In another example, the significance test may require that the longest perpendicular be at least 10% of the value of the appropriately normalized height and width of the histogram added in quadrature. The height and width may be differently normalized to provide different weighting. Whilst a default fraction, such as 5% or 10%, may be used, the fraction may also be changed to better suit a particular application and expected histogram characteristics. A determined visualization threshold which lies within a signal value range representing a single tissue type will fail an appropriately configured significance test. Boundaries associated with these visualization thresholds will be noted as cosmetic boundaries and will be ignored by selection tools.

Figure 5D:
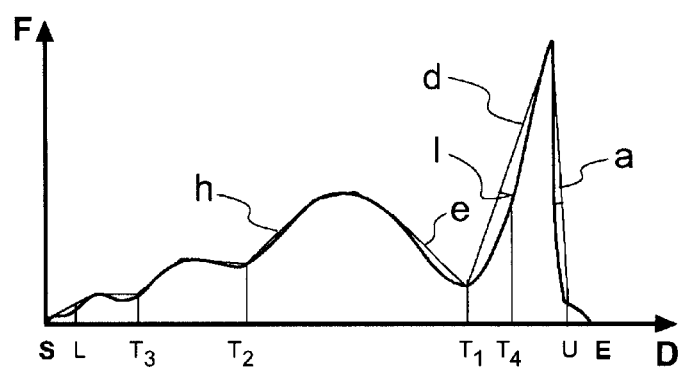
FIG. 5d shows a histogram of data values within a VOI within a 3D data set and to which a fourth convex hull has been applied to determine a fourth visualization threshold.

FIG. 5d shows the histogram previously shown in FIG. 3, but on which the fourth (i.e. $n^{th}$ where n=4) convex hull associated with attempting to find a fourth visualization threshold $T_4$ is shown. The fourth convex hull meets the histogram at signal values $T_1$, $T_2$ and $T_3$. As noted above, the three previously identified visualization thresholds, and hence associated color boundaries, define four voxel value sub-ranges in the histogram. As further noted above, the histogram example shown in FIG. 3 corresponds to a VOI containing four distinct tissue types and accordingly there are no more significant visualization thresholds to be identified. This is reflected by the fact that the longest perpendicular which can be drawn between the convex hull and the histogram shown in FIG. 5d (marked by the line l) is relatively small compared with the lines c, g and k used to define the visualization thresholds $T_1$, $T_2$ and $T_3$ and shown in FIGS. 5a, 5b and 5c respectively. The visualization threshold $T_4$ defined by the line l shown in FIG. 5d is thus not significant and would fail an appropriately configured significance test.

Where a visualization threshold is deemed not to be significant, for example with reference to a model of a histogram's expected characteristics or by comparison with a pre-determined minimum length of longest perpendicular, it can either be noted as such to provide a cosmetic color boundary in the color table (and given an appropriate sharpness value of, for example, 0), or it can be discarded. The concept of a cosmetic boundary is a boundary which is defined in the color table and thus relevant for display purposes, but which is ignored by other tools in the graphics system which are boundary sensitive, such as tools used for selecting objects that contain algorithms that automatically search for and mark boundaries. One or more cosmetic boundaries may be determined iteratively in the manner described above until sufficient number are determined to satisfy the requirements of the number of available displayable color ranges (i.e. j–1 color boundaries for j displayable color ranges).

If color boundaries associated with visualization thresholds which fail the significance test are to be discarded, rather than kept but marked as cosmetic, the iterative search for further visualization thresholds may cease after the first significance-test-failing visualization threshold is identified. In these circumstances there will be fewer identified voxel value sub-ranges in the histogram (which nominally correspond to fewer distinct tissue types within the VOI) than there are displayable color ranges. Individual color ranges may be allotted to the individual signal value ranges defined by the identified color boundaries and the remaining color ranges unused, or cosmetic boundaries can be artificially defined. For example, a cosmetic boundary could be generated by defining a color boundary mid-way between the two signal values of the most widely separated significant color boundaries. If multiple cosmetic boundaries are to be defined, the signal values with which to associate them can be determined serially, i.e. one after another using the above criterion, or in parallel such that they collectively divide the widest signal value range in to equal sections.

The significance of a given color boundary may be a continuous parameter and need not be a purely binary—e.g. a color boundary need not simply be significant or non-significant (i.e. non-cosmetic or cosmetic). As noted above, sharpness values derived form a significance parameter may be used as a direct measure of a boundary's significance such that in many cases the sharpness value itself will be used to directly indicate a boundary's significance. Accordingly, significance may be given an insignificant level (e.g. 0) and one or more levels of significance (e.g. integers between 1 and 100). This facility may be used by other graphics tools within the image processing system, for example to determine the probability of a boundary being significant when attempting to resolve conflicts when determining the bounds of a topological entity. A zero level of sharpness (i.e. significance) is set for boundaries which fail the significance test.

As indicated above, the visualization threshold's significance could be based on the length of the appropriately normalized length of the perpendicular between the $n^{th}$ convex hull and the histogram. By indicating to a user the significance of the identified color boundaries used in the display, the interpretation of the displayed image can be aided. The significance of each of the color boundaries may also play a role in the appropriate use of connectivity algorithms used to define surfaces or volumes within the 3D data set which are associated with features identified by a user in the projected image.

Figure 6:
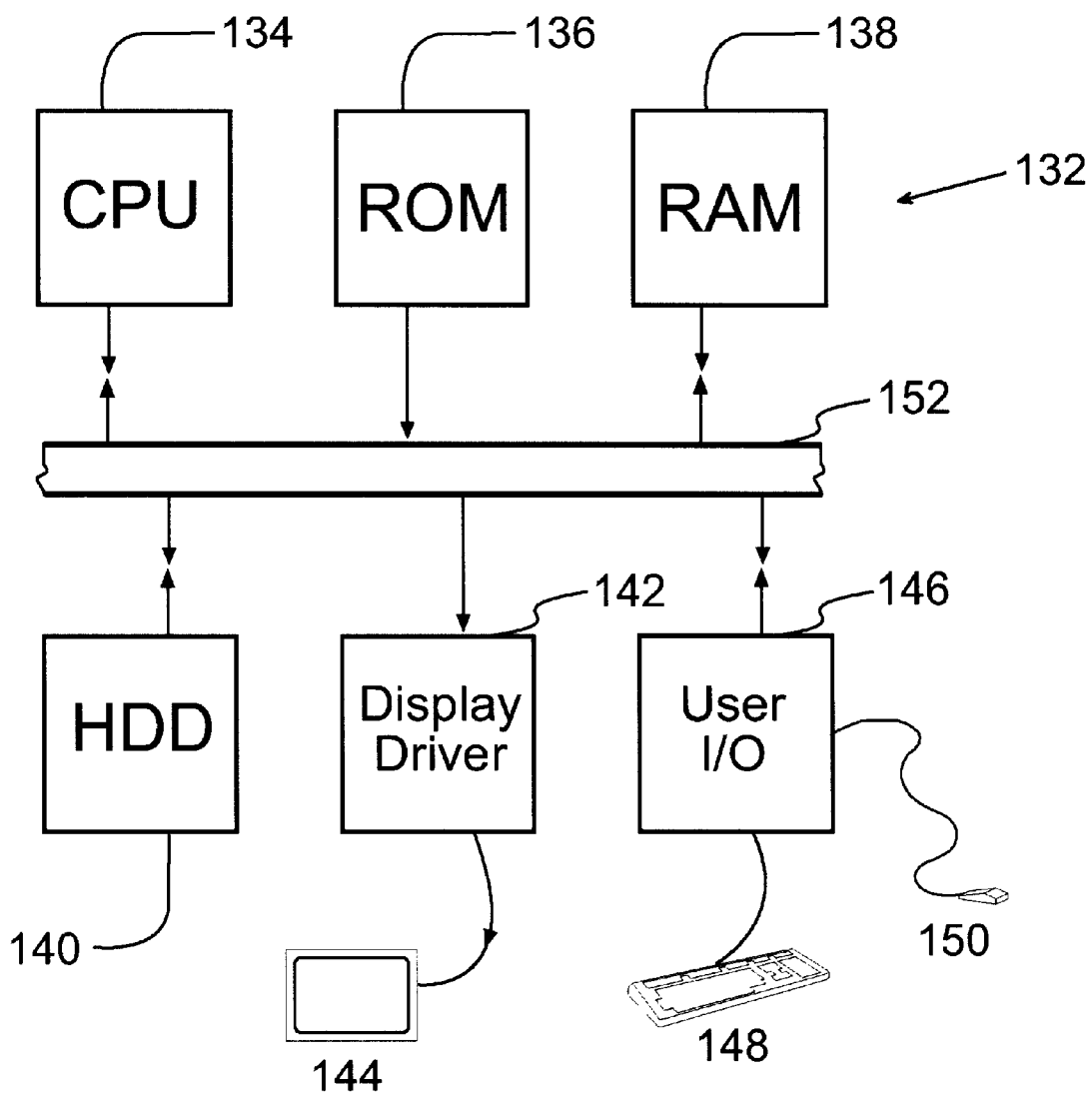
FIG. 6 shows a computer system for storing, processing and displaying medical image data.

FIG. 6 schematically illustrates a general purpose computer 132 of the type that may be used to perform processing in accordance with the above described techniques. The computer 132 includes a central processing unit 134, a read only memory 136, a random access memory 138, a hard disk drive 140, a display driver 142 and display 144 and a user input/output circuit 146 with a keyboard 148 and mouse 150 all connected via a common bus 152. The central processing unit 134 may execute program instructions stored within the ROM 136, the RAM 138 or the hard disk drive 140 to carry out processing of signal values that may be stored within the RAM 138 or the hard disk drive 140. Signal values may represent the image data described above and the processing may carry out the steps described above and illustrated in FIG. 4. The program may be written in a wide variety of different programming languages. The computer program itself may be stored and distributed on a recording medium, such as a compact disc, or may be downloaded over a network link (not illustrated). The general purpose computer 132 when operating under control of an appropriate computer program effectively forms an apparatus for processing image data in accordance with the above described technique. The general purpose computer 132 also performs the method as described above and operates using a computer program product having appropriate code portions (logic) for controlling the processing as described above.

The image data could take a variety of forms, but the technique is particularly well suited to embodiments in which the image data comprises a collection of 2D images resulting from CT scanning, MRI scanning, ultrasound scanning or PET that are combined to synthesize a 3D object using known techniques. The aided visualization of distinct features within such images can be of significant benefit in the interpretation of those images when they are subsequently projected into 2D representations along arbitrarily selected directions that allow a user to view the synthesized 3D object from any particular angle they choose.

Having described the principles of a method for automatically determining presets, specific examples of its application will now be given. In some applications, presets may be required to satisfy further conditions before they are accepted for defining color range boundaries (or other visualization parameters). For example, in applications where bone visualization within a CT data set is of prime interest, preset thresholds should not be defined between those signal values representing soft tissue and blood vessels since both of these should be made transparent in the displayed image. Instead, less significant but more appropriate thresholds within the range of signal values representing bone may be preferred.

First Example—"Active MR Preset"

Magnetic resonance imaging (MR) data sets are generally un-calibrated and display a wide range of data-values, dependent on, for example, acquisition parameter values or the position of the VOI with respect to a scanner's detector coils during scanning. Accordingly, it is not usually possible to pre-estimate suitable signal values with which to attribute color range presets and this makes the present invention especially useful for application to MR data sets.

Figure 7A:
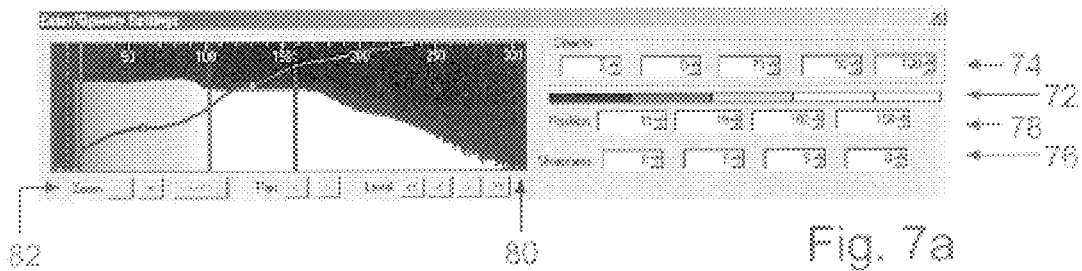
FIG. 7a shows a visualization state tool loaded with a VOI from a 3D data set for which color boundaries have been determined according to an automatic preset according to a first example of the invention, referred to as "Active MR"

FIG. 7a schematically shows the appearance of a visualization state tool displayed on the display 144 shown in FIG. 6. The display tool shows a user the outcome of a preset determination method for a selected VOI. The visualization state tool comprises a data display window 80, a color display bar 72, a display of opacity values 74, a display of boundary positions 78, a display of sharpness values 76 and a number of display modification buttons 82. The color display bar identifies the five color ranges available for display in this application, although no details of the available shades within each range are shown. The display of boundary positions 78 shows the signal values of the four determined color boundaries. The individual display windows for each of these four boundary positions are centered beneath the two color ranges indicated on the color display bar 72 with which each is associated. The display of sharpness values 76 can be used to determine the significance of the four determined boundaries. The display of opacity values 74 at each of the boundary positions (and at the maximum signal value) is also shown (with example values 0, 0, 73, 90, 100).

The data display window shows a logarithmically scaled histogram of the signal values for the entire 3D data set overlaid with dashed and solid vertical lines marking the cosmetic and significant boundary positions respectively. The boundary lines may also be marked differently, for example based upon their relative significance. The histogram is colored to represent the color table and opacity mapping at each signal value indicated by the scale along the top of the data display window. The frequency distribution shown here is that of the entire image data set and is not restricted to the VOI on which the preset determination is based. In some cases it may aid a user's interpretation if the histogram of the selected VOI is shown. This might be in place of the histogram of the entire data set or indicated separately, such as in a separate window or drawn as a curve overlaying the entire image data set histogram. A curve is plotted overlaying the frequency distribution which shows the opacity curve. The opacity curve is formed by interpolation between the opacity values set for each of the color boundary positions taking into account the sharpness at each boundary, in this example 0, 0, 73, 90 and 100 for voxel values 11, 19, 102, 158 and the maximum voxel value respectively. The display modification buttons 82 allow a user to pan along the histogram shown in the display window and also allows for repositioning color boundaries if required.

The color boundaries shown in the display of boundary positions 78 in FIG. 7a have been determined to attempt to best show what the user wants to see within the currently selected VOI. In some circumstances, for example when supplied with a VOI which includes the whole volume, the preset determination method might be configured to automatically assume that it is the tissue/air interface which is required to be visualized. Accordingly, after determining the presets, the voxels containing signal values below the lowest significant threshold will be assumed to represent air and be made transparent in the projection. If the VOI is selected such that only a small proportion of air is included, the preset determination method will look for a higher threshold of apparent significance to determine which voxels should be made transparent. As noted above, the intensities in MR vary substantially across the imaged volume due to coil positioning and other factors, so the smaller the VOI then the more accurate/useful the resulting visualization is likely to be.

When applied to an MR data set, the active preset determination method of this example first tries to find a candidate threshold, using the technique described above, and which further satisfies the condition that 60% (+/−30%) of the volume is transparent.

In this example, a suitable threshold is found to be at signal value 15. However, the design of the "Color/Opacity Settings" interpolation used by the particular display software used in this example operates best if two boundaries are placed a small distance on either side of the computed background threshold in order to provide a rapid rise in the opacity curve as usually desired. In this example, these two boundaries are placed at positions ±4 signal value units either side of the visualization threshold at signal values of 11 and 19 respectively. The boundaries may also be placed at other positions, for example, at positions ±3 signal value units either side of the visualization threshold.

Since in this example there are five color ranges to allot (requiring four color boundaries), the method looks for up to two more candidate visualization thresholds above the background level, at which to place the two remaining color boundaries. If two significant visualization thresholds cannot be found, then the missing color boundaries are placed in the center of the largest gap, but, as noted above, the associated sharpness (i.e. significance) is set to 0, indicating a cosmetic boundary with no significance to selection.

In this example, a second visualization threshold at signal value position 102 is determined to be significant and a single color boundary with a sharpness set to 5 is defined at signal value position 102. No further significant visualization thresholds are found and the remaining color boundary, between yellow and white, is placed at signal value position 158. It should be noted that, whilst not immediately apparent from the histogram shown in the data display window 80, this cosmetic boundary is in the middle of the widest gap between significant color boundaries. There are two reasons why it is perhaps not immediately apparent. Firstly, the histogram upon which the analysis is made differs from the histogram shown in the data display window since the former is restricted to the VOI and un-sculpted domain whereas the latter represents the entire 3D data set. Secondly, as noted above, in order to prevent the analysis from being thrown off by spurious values in the tails of the distribution, the lowest and highest 0.1% of voxels are excluded from the numerical analysis. Because the histogram shown in the dialog has a logarithmic vertical scale the voxels at the extremes of the voxel value range can appear more significant.

Figure 7B:
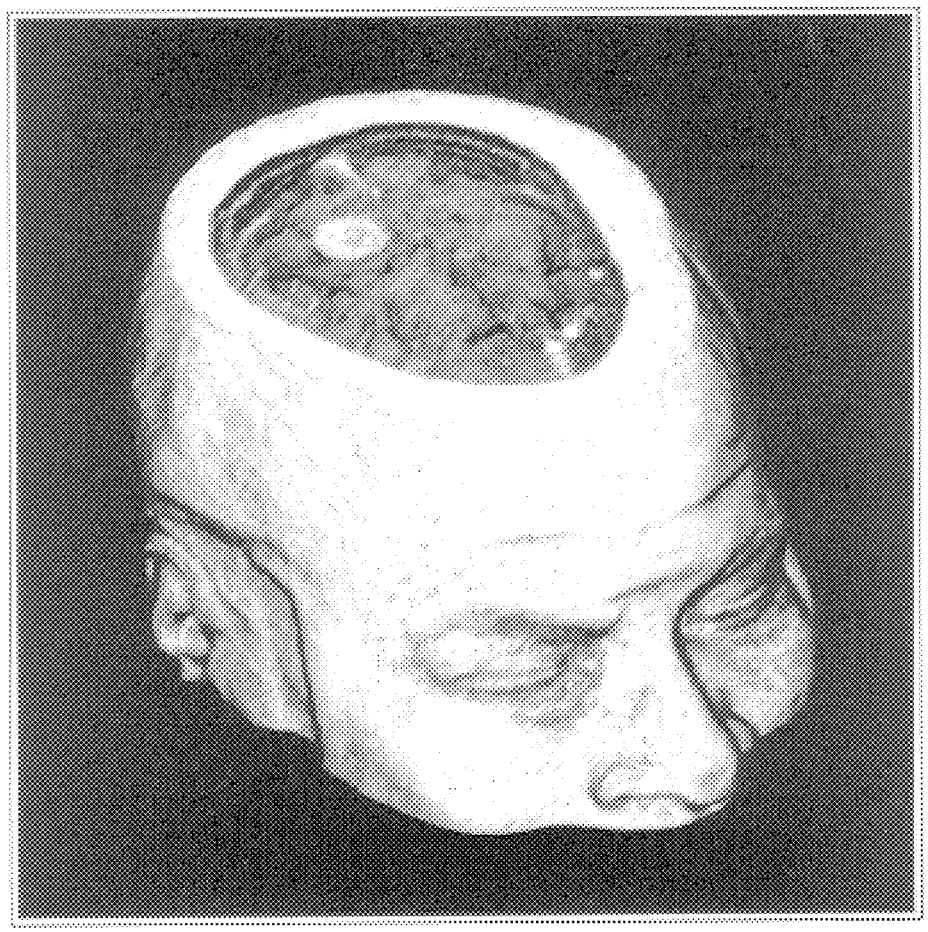

FIG. 7b shows an example image displayed according to the automatic preset of FIG. 7a. The air/tissue interface is shown with regions of skin, bone and soft tissue are apparent in the image.

Second Example—"Active CT Preset"

In this example, the same preset type is used as in the first example. This may be useful for CT data sets in which a user wants to visualize soft tissue.

Third Example—"Active Bone (CT) Preset"

This example is for use on CT data sets for the purpose of visualizing and selecting bone.

Figure 8A:
FIG. 8a shows a visualization state tool loaded with a VOI from a 3D data set for which color boundaries have been determined according to an automatic preset according to a second example of the invention, referred to as "Active Bone (CT)"

FIG. 8a schematically shows the appearance of a visualization state tool presenting an example of use of the "Active Bone (CT)" Preset. The different fields within the visualization state tool shown in FIG. 8a will be understood from the description of FIG. 7a.

The "Active Bone (CT) Preset" operates by determining a first significant visualization threshold within the signal value range 70 HU to 270 HU. In the example, a visualization threshold value of 182 HU is determined. If no such visualization threshold is found then 170 HU is used. This first visualization threshold is used to set the background level in the display software by setting two boundary positions at ±45 HU from the first visualization threshold. The boundary positions in this example are accordingly at 137 HU and 227 HU. With the five available ranges of color indicated in FIG. 8a there are two remaining presets to determine. One of these is placed at −500 HU (which, in the "Active Bone" scheme, is denoted as a significant boundary with a sharpness of 5 to show some information about soft tissue in the side multi-planar reconstruction (MPR) views. A fourth color boundary is placed at 600 HU to give some intensity information. The fourth color boundary is ascribed a sharpness value of 0 to denote a cosmetic boundary.

Figure 8B:
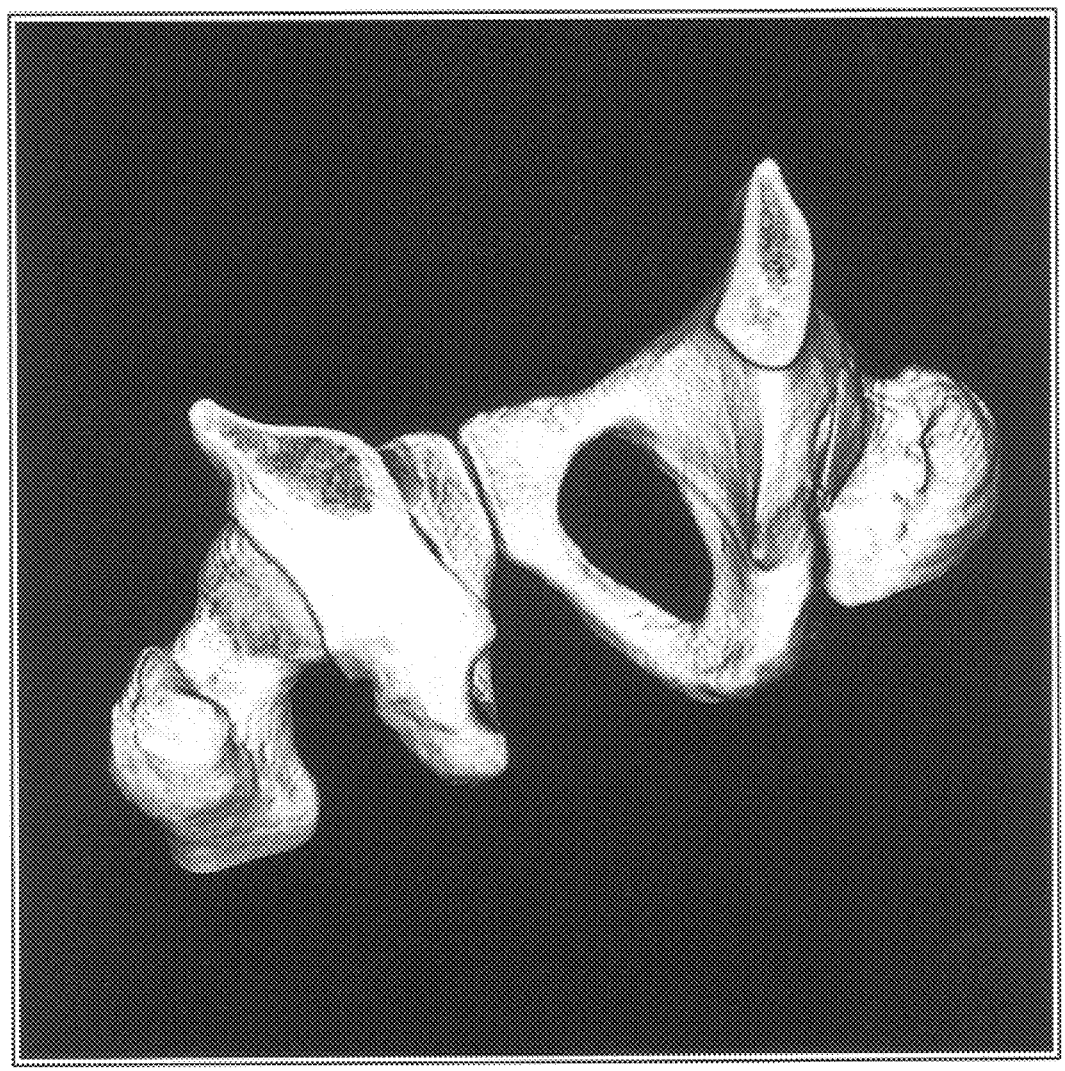

FIG. 8b shows an example image displayed according to the automatic preset of FIG. 8a. Regions of bone are most apparent in the image.

Fourth Example—"Active Angio (CT) Preset"

This preset assumes the data are in correctly calibrated Hounsfield units. The purpose of this preset is to visualize angio-tissue.

Figure 9A:
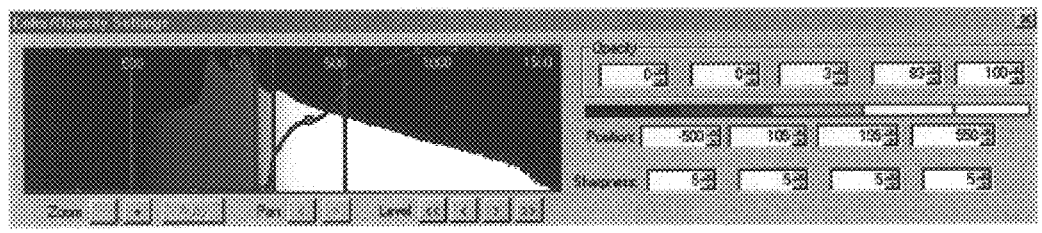
FIG. 9a shows a visualization state tool loaded with a VOI from a 3D data set for which color boundaries have been determined according to an automatic preset according to a third example of the invention, referred to as "Active Angio (CT)"

FIG. 9a schematically shows the appearance of a visualization state tool presenting an example of use of the "Active Angio (CT)" Preset. The different fields within the visualization state tool shown in FIG. 9a will be understood from the description of FIG. 7a.

The yellow/white boundary is placed at a position determined by the histogram analysis within the range 550 HU±200 HU, and this boundary is given a sharpness of 5 so that is significant to selection. In the example a boundary position of 550 HU is determined. Thus, in good data sets, the selection tools can be used in conjunction with this preset to discriminate bone from contrast enhanced vasculature.

The other boundary positions are fixed at values −500 HU, 105 HU and 195 HU.

Figure 9B:
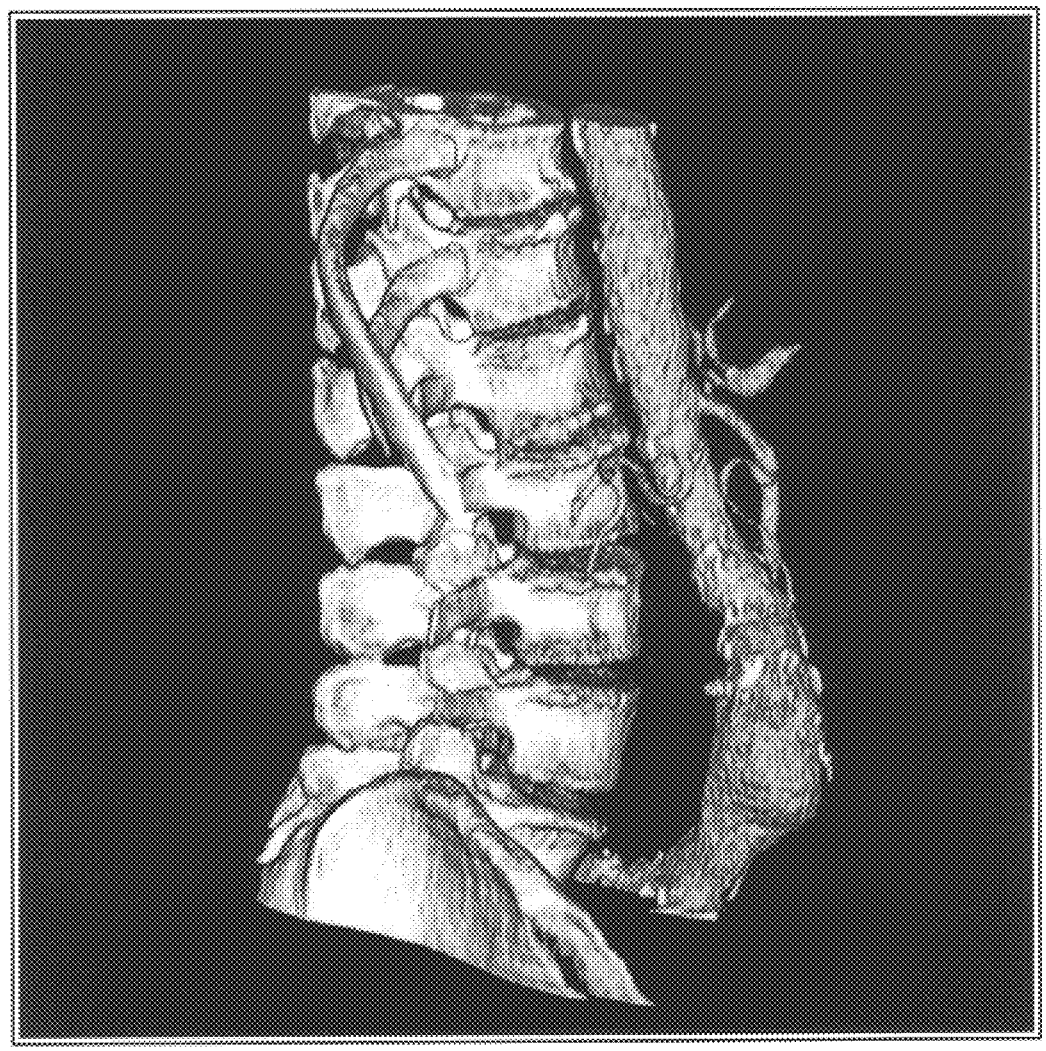

FIG. 9b shows an example image displayed according to the automatic preset of FIG. 9a. Regions of bone and angio-tissue are most apparent in the image.

Summary

It should be clear from the above examples that the preset determination method of the present invention can be specifically tailored in any number of ways to apply to data sets with known specific characteristics. The method can also be used as an entirely general tool with no prior knowledge of the data set, such as in the MR example described above. In addition, users may themselves customize the preset determination to suit the requirements of a particular study. This might be done, for example, where CT calibrated data are used and a user requires features with a particular X-ray attenuation to be identified. This might also be done to distinguish between two tissue types of similar X-ray attenuations. Similarly, with un-calibrated data, a user might modify the preset determination method based on the appearance of a single 2D projection so that the preset is applied consistently to all 2D projections generated from that voxel data set. By storing parameters associated with a user's personal customizations to the method (such as the significance test stringency, the typical fraction of the data set the user wants to appear as transparent, or specific signal value ranges in which thresholds should occur), the modified method could be consistently applied to further data sets.

While by way of example the foregoing description is directed mainly towards determining visualization thresholds which are used to define color boundaries, it will be appreciated that determined visualization thresholds are equally suitable for defining boundaries for visualization parameters other than color, such as opacity, that are relevant for rendering. Furthermore, it is often clinically useful for the placement of boundaries in an opacity mapping to be positioned at the same signal values as the boundaries in a color mapping. Other visualization parameters for which the invention could be used include rate of change of color with signal value, rate of change of opacity with signal value, and segmentation information.

The preset determination is also not limited to finding any particular number of boundaries, and the associated number of visualization thresholds, but is extendable to determining any number of boundaries or visualization thresholds. In some applications it may be appropriate to determine more visualization thresholds than there are distinct boundaries required to allow less significant thresholds to play a role in defining the specific allocation of available color shades or transitions between colors within one or more of the determined ranges, for example.

It will be appreciated that although particular embodiments of the invention have been described, many modifications/additions and/or substitutions may be made within the spirit and scope of the present invention.

What is claimed is:

1. A method of setting visualization parameter boundaries for displaying an image from a 3D data set comprising a plurality of voxels, each with an associated signal value, comprising:

selecting a volume of interest (VOI) within the 3D data set;

generating a histogram of signal values from voxels that are within the VOI;

applying a numerical analysis method to the histogram to determine a visualization threshold; and setting at least one of a plurality of boundaries for a visualization parameter according to the visualization threshold.

2. The method of claim 1, wherein a first visualization parameter boundary is set at the visualization threshold.

3. The method of claim 1, wherein first and second visualization parameter boundaries are set either side of the visualization threshold.

4. The method of claim 1, wherein the numerical analysis method is applied iteratively to the histogram to determine a plurality of visualization thresholds and corresponding visualization parameter boundaries.

5. The method of claim 1, further comprising applying a significance test to visualization thresholds and, according to the outcome of the significance test, ascribing a significance marker for those ones of the voxels having signal values at or adjacent to the visualization threshold, wherein the significance marker indicates significance or insignificance of the visualization threshold.

6. The method of claim 5, further comprising applying a selection tool to the 3D data set, wherein the selection tool is sensitive to the significance markers.

7. The method of claim 6, wherein the selection tool ignores visualization parameter boundaries that have been marked as insignificant.

8. The method of claim 1, wherein the numerical analysis method comprises:

forming a convex hull of a plurality of segments around the histogram;

determining which perpendicular from the segment to the histogram has the greatest length; and taking the signal value at the intersection between the histogram and the perpendicular as the visualization threshold.

9. The method of claim 1, wherein the numerical analysis method comprises:

forming a convex hull of a plurality of segments around the histogram;

determining which perpendicular from the segment to the histogram has the greatest length; and taking the signal value at the intersection between the histogram and the perpendicular as the visualization threshold, wherein the method further comprises:

applying a significance test based on the length of the perpendicular determined to have the greatest length to the visualization threshold and, according to the outcome of the significance test, ascribing a significance marker for those ones of the voxels having signal values at or adjacent to the visualization threshold, wherein the significance marker indicates significance or insignificance of the visualization threshold.

10. The method of claim 9, wherein the visualization threshold is determined to be insignificant if the ratio of the length of the perpendicular to a parameter derived from the signal value range and/or the frequency range of the histogram is below a minimum score.

11. The method of claim 1, wherein the numerical analysis method is applied to the histogram within a predetermined restricted range of signal values to search for a visualization threshold within that restricted range.

12. The method of claim 11, wherein the restricted range is defined in terms of Hounsfield units.

13. The method of claim 1, further comprising displaying to a user the histogram and its visualization parameter boundaries together with the image created from the 3D data set, so that the user is made aware of the visualization parameter boundaries.

14. The method of claim 1, wherein the histogram is restricted to un-sculpted voxels in the VOI.

15. The method of claim 1, wherein voxels with the highest and/or the lowest signal values are excluded from the numerical analysis method.

16. The method of claim 1, wherein the visualization parameter is color.

17. The method of claim 1, wherein the visualization parameter is opacity.

18. The method of claim 1, wherein the visualization parameter is rate of change of color with signal value.

19. The method of claim 1, wherein the visualization parameter is rate of change of opacity with signal value.

20. The method of claim 1, wherein the visualization parameter is segmentation information.

21. The method of claim 1, wherein the 3D data set is a medical imaging data set.

22. The method of claim 1, further comprising selecting a sub-set of voxels within the 3D data set, wherein the step of selecting a sub-set of voxels is based upon the visualization parameter boundaries.

23. The method of claim 1, further comprising generating a second histogram of signal values from all of the voxels that are within the 3D data set.

24. The method of claim 23, wherein a display of the second histogram is provided on a visual display unit.

25. A computer program product bearing computer readable instructions for performing the method of claim 1.

26. A computer apparatus loaded with computer readable instructions for performing the method of claim 1.

* * * * *